US012807556B2

(12) United States Patent
Sharma et al.

(10) Patent No.: US 12,807,556 B2
(45) Date of Patent: Nov. 24, 2026

(54) PROCESS FOR THE PREPARATION OF PROPOFOL

(71) Applicant: FRESENIUS KABI ONCOLOGY LTD., New Delhi (IN)

(72) Inventors: Ashwani Kumar Sharma, Haryana (IN); Manish Pandey, Haryana (IN); Abhishek Giri, Haryana (IN); Sarbjot Singh Sokhi, Haryana (IN); Govind Singh, Haryana (IN); Saswata Lahiri, Haryana (IN); Walter Cabri, Bologna (IT)

(73) Assignee: Fresenius Kabi Oncology Ltd., New Delhi (IN)

( * ) Notice: Subject to any disclaimer, the term of this patent is extended or adjusted under 35 U.S.C. 154(b) by 941 days.

(21) Appl. No.: 17/906,677

(22) PCT Filed: Mar. 25, 2021

(86) PCT No.: PCT/IB2021/052471

§ 371 (c)(1),
(2) Date: Sep. 19, 2022

(87) PCT Pub. No.: WO2021/191832

PCT Pub. Date: Sep. 30, 2021

(65) Prior Publication Data

US 2023/0174444 A1 Jun. 8, 2023

(30) Foreign Application Priority Data

Mar. 26, 2020 (IN) ............................ 202011013179

(51) Int. Cl.
*C07C 37/50* (2006.01)
*C07C 39/06* (2006.01)

(52) U.S. Cl.
CPC ............. *C07C 37/50* (2013.01); *C07C 39/06* (2013.01)

(58) Field of Classification Search
CPC ............................... C07C 37/50; C07C 39/06
See application file for complete search history.

(56) References Cited

FOREIGN PATENT DOCUMENTS

| | | | |
|---|---|---|---|
| CN | 101 475 450 | B | 7/2011 |
| CN | 106588576 | A | 4/2017 |
| IN | 336365 | | 4/2020 |
| JP | H03-232833 | A | 10/1991 |
| JP | H09-241199 | A | 9/1997 |
| SU | 443019 | A1 | 9/1974 |
| WO | WO 2011/161687 | A1 | 12/2011 |
| WO | WO 2013/035103 | A1 | 3/2013 |

OTHER PUBLICATIONS

Kolka et al., "The ortho-Alkylation of Phenols," *J. Org. Chem.* 21(6): 712-713 (1956).

Pramanik et al., "Commercial Manufacturing of Propofol: Simplifying the Isolation Process and Control on Related Substances," *Organic Process Research & Development* 18(1): 152-156 (2014).

European Patent Office, International Search Report in International Application No. PCT/IB2021/052471 (Jun. 25, 2021).

European Patent Office, Written Opinion in International Application No. PCT/IB2021/052471 (Jun. 25, 2021).

International Bureau of WIPO, International Preliminary Report on Patentability in International Application No. PCT/IB2021/052471 (Sep. 22, 2022).

*Primary Examiner* — Adam C Milligan
*Assistant Examiner* — Karen Cheng
(74) *Attorney, Agent, or Firm* — Leydig, Voit & Mayer, Ltd.

(57) ABSTRACT

The present provides a simple, convenient and time-efficient process for the preparation of propofol. Particularly, the present invention provides an improved process for the preparation of propofol using a heterocyclic base for the decarboxylation reaction. The present invention provides a time-efficient process for the preparation of propofol with high yield and purity.

15 Claims, No Drawings

PROCESS FOR THE PREPARATION OF PROPOFOL

CROSS-REFERENCE TO RELATED APPLICATIONS

This patent application is the U.S. national stage of International Patent Application No. PCT/IB2021/052471, filed on Mar. 25, 2021, which claims the benefit of Indian Patent Application number 202011013179, filed Mar. 26, 2020, the disclosures of which are incorporated herein by reference in their entireties for all purposes.

FIELD OF THE INVENTION

The present invention relates to an improved process for the preparation of a compound of formula I (propofol), Formula I

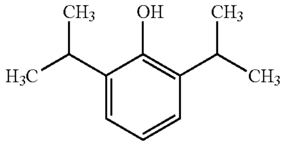

Specifically, the present invention relates to a time-efficient process for the preparation of propofol with high yield and purity.

BACKGROUND OF THE INVENTION

Propofol is chemically known as 2,6-diisopropylphenol, and is a short-acting, intravenously administered sedative hypnotic agent for induction and maintenance of anesthesia or sedation. Intravenous injection of a therapeutic dose of propofol induces hypnosis, with minimum excitation, usually within 40 seconds from the start of the injection.

Propofol is administered intravenously, therefore, it is imperative that the administered product be free from associated impurities and have high purity. For pharmaceutical purposes, ideal purity for propofol should be more than 99.9%. The commercially available propofol is about 97% pure, which is low for use as an active pharmaceutical ingredient (API). Many processes for the synthesis and purification of propofol are associated with the formation of various impurities and require longer reaction time.

Propofol is generally prepared by the alkylation of propene with phenol (e.g. A. J. Kolka, J. P. Napolitano, G. G. Ecke: *The ortho-Alkylation of Phenols*. In: *J. Org. Chem.* 21 (6), 1956, S. 712-713). This procedure is associated with serious drawbacks since the yield of propofol is quite low and it requires high pressure and high temperature. Moreover, the product has to undergo a complicated separation procedure because the reaction product is a mixture of regioisomers, thus affecting the purity of the product. The major contaminants being 2,4- and 2,5-diisopropylphenol, 2,4,6-triisopropyl phenol, and 1-isopropoxy-2,4-diisopropylbenzene, have small differences in their boiling points. These impurities are difficult to remove.

Another method for the preparation of propofol is decarboxylation of 4-hydroxy-3,5-diisopropylbenzoic acid intermediate, as disclosed in SU443019.

SU443019 discloses a process for the preparation of propofol by decarboxylation of 4-hydroxy-3,5-diisopropylbenzoic acid in the presence of triethylamine at a temperature of 120-140° C. for one hour; however, this reaction does not complete in one hour due to the low boiling point of triethylamine (approx. 89° C.). During the process, violent carbon dioxide bubbles are observed, and the process requires a flask equipped with a downward Liebig condenser to distil off triethylamine. This process results in number of impurities, which are difficult to remove from the final API.

WO2011161687 discloses a process for the preparation of propofol by decarboxylation of 4-hydroxy-3,5-diisopropylbenzoic acid in ethylene glycol and sodium hydroxide pellets at 140-145° C. for 7 hours. The process requires five times dilution with water, pH adjustments and three times extraction with toluene. Even after multiple dilutions and extractions with organic solvent, the process further involves washing with aq. sodium bicarbonate solution and water. This makes the process time consuming, tedious, and unfavourable for commercial manufacturing. Also, the ethylene glycol solvent used in the process is highly flammable and thus requires proper monitoring of the reaction.

WO2013035103 also discloses a similar process for the preparation of propofol by decarboxylation of 4-hydroxy-3,5-diisopropylbenzoic acid in ethylene glycol and sodium hydroxide for 7 hours.

Ethylene glycol is a toxic solvent and has a high boiling point. Use of a high boiling solvent makes the process difficult during the workup, especially for the removal of the solvent. Due to the higher boiling point (197° C.) of ethylene glycol, it interferes during purification of the crude propofol by high-vacuum distillation and poses additional threat for the residual solvent test (ICH limit for ethylene glycol NMT=620 ppm).

CN106588576 discloses decarboxylation of 4-hydroxy-3,5-diisopropylbenzoic acid using a decarboxylation enzyme in buffer and the reaction is carried out at ambient temperature for 15 hours to give propofol with 80% yield. This process takes about 15 hours to complete the reaction. Such a long reaction time is unfavourable for commercial manufacturing.

IN 1420/MUM/2012 discloses a process for the synthesis of propofol by decarboxylation of 4-hydroxy-3,5-diisopropylbenzoic acid in 2-ethoxyethanol and sodium hydroxide at high temperature. Similar to the above-mentioned patents and applications, this application also discloses the use of a high boiling solvent, ethoxyethanol, for the decarboxylation reaction.

In view of the above drawbacks in the preparation of propofol, there remains a need to improve such processes and develop an efficient, simple, cost-effective and industrially viable synthetic route, which can overcome the drawbacks of the prior art(s) related to synthesis of propofol. It is important to develop a method that avoids the use of high boiling solvents, flammable solvents, multiple washings, and a long reaction time.

The present invention describes an improved process for the synthesis of propofol, allows the reaction to complete in a shorter time, and fulfills the requirement of high yield and high purity.

OBJECT OF THE INVENTION

An object of the present invention is to provide an improved process for the preparation of propofol.

Yet another object of the present invention is to provide a time-efficient and cost-effective process for the preparation of propofol.

SUMMARY OF THE INVENTION

An aspect of the present invention is to provide an improved process for the preparation of a compound of formula I (propofol), Formula I

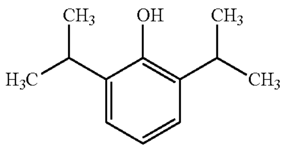

comprising the step of decarboxylating 4-hydroxy-3,5-diisopropylbenzoic acid of formula II, Formula II

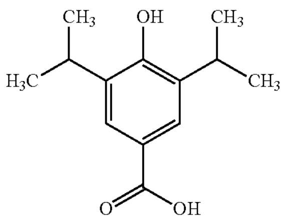

in the presence of a heterocyclic base.

Another aspect of the present invention is to provide a pharmaceutical composition comprising a therapeutically effective amount of propofol, prepared by the process of the present invention, along with pharmaceutically acceptable excipients(s)/carrier(s).

DEFINITIONS

The following definitions are used in connection with the present application, unless it is indicated otherwise.

The term "ambient temperature" refers to a temperature ranging from about 15° C. to 35° C., preferably to a temperature ranging from about 20° C. to 30° C., more preferably to a temperature of 20° C.-25° C.

The term "heterocyclic base" as used herein refers to an optionally substituted nitrogen-containing heterocyclic compound, which can act as an organic base during the reaction. The heterocyclic base includes imidazole, imidazole derivatives, piperazine, pyrimidine, and the like.

The term "imidazole derivative" as used herein refers to imidazole substituted with an alkyl group, e.g. 2-methylimidazole, 2-ethylimidazole.

The term "alkyl" as used herein refers to a hydrocarbon-based group that may be linear or branched and may be saturated or unsaturated. In particular, the alkyl group contains 1 to 10 carbon atoms such as methyl, ethyl and the like.

The term "mineral acid" as used herein refers to an inorganic acid, optionally an aqueous mineral acid, which does not comprise any carbon atoms, and includes hydrochloric acid, sulfuric acid, perchloric acid and the like. As used herein, the term "aqueous mineral acid" includes aqueous hydrochloric acid, aqueous sulfuric acid, and aqueous perchloric acid. The preferred aqueous mineral acid is aqueous sulfuric acid.

The term "alcohol" as used herein refers to an organic compound in which one or more hydroxyl (OH) groups are attached to carbon atoms (C) instead of hydrogen atoms (H). In particular, the alcohol contains 1-6 carbon atoms. Examples of alcohols include methanol, ethanol, n-propanol, isopropanol, butanol, tert-butanol, pentanol, hexanol and the like.

The term "aromatic hydrocarbon" as used herein refers to hydrocarbons that have at least one aromatic ring. Examples of aromatic hydrocarbons include toluene, anisole, o-xylene, m-xylene, p-xylene and the like.

The term "halogenated solvents" as used herein refers to solvents containing one or more halogen atom. Example of halogenated solvents include dichloromethane, dichloroethane, chloroform, carbon tetrachloride and the like.

The term "ester solvents" as used herein refers to organic solvents having an ester group in their molecular structures. Examples of ester solvents include ethyl acetate, methyl acetate, n-butyl acetate, isobutyl acetate, sec-butyl acetate, isopropyl acetate and the like.

All ranges recited herein include the endpoints, including those that recite a range between two values. Whether indicated or not, all values recited herein are approximate as defined by the circumstances, including the degree of expected experimental error, technical error, and instrument error for a given technique used to measure value.

ABBREVIATIONS

HPLC High Performance Liquid Chromatography

DETAILED DESCRIPTION OF THE INVENTION

The present invention relates to a process for the preparation of a compound of formula I (propofol), Formula I

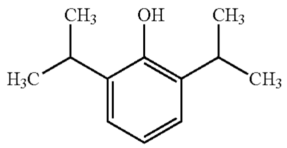

In an embodiment, the process comprises the step of decarboxylating 4-hydroxy-3,5-diisopropylbenzoic acid of formula II, Formula II

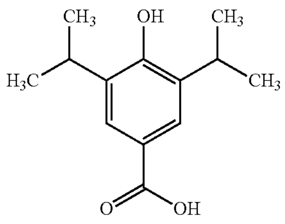

in the presence of a heterocyclic base.

The heterocyclic base used in the decarboxylation may be selected from imidazole, imidazole derivatives, piperazine and pyrimidine. Preferably, the reaction is carried out in the presence of imidazole as a base. The reaction may be carried out at a temperature in the range of 120-170° C., preferably at a temperature in the range of 130-160° C., most preferably 145-155° C. The decarboxylation reaction is completed in 30 minutes to 3.5 hours, preferably 30 minutes to 3 hours, more preferably within 1 to 2 hours.

In one embodiment, the decarboxylation reaction is carried out in the presence of a solvent. The solvent may be selected from the group consisting of aromatic hydrocarbon solvents, being preferably anisole, toluene or a mixture thereof.

Surprisingly, the decarboxylation reaction can also be carried out without a solvent. Solvent-free decarboxylation is especially advantageous as it allows to carry out the reaction in small volume vessels, which renders the synthesis more cost efficient. Therefore, another embodiment is solvent-free decarboxylation of the compound of formula II in the presence of a heterocyclic base such as imidazole, an imidazole derivative, piperazine, or pyrimidine, preferably imidazole.

It was surprisingly found that the process according to the present invention leads to significantly higher yield and purity than that obtained by the above-mentioned prior art processes.

In addition, the process according to the present invention accelerates the reaction process substantially. The decarboxylation reaction is completed significantly faster than the procedures discussed in prior arts, resulting in considerable cost savings, e.g. because of shorter facility use.

Propofol may be extracted from the reaction mixture by the addition of a solvent selected from the group consisting of water, aromatic hydrocarbon solvents, halogenated solvents, ester solvents and mixture thereof. Preferably, the product is extracted from reaction mixture by addition of water and aromatic hydrocarbon solvents. The product may be isolated from the reaction mixture using conventional method such as evaporation of solvent, distillation, the concentration of solvent or combination thereof. Preferably, propofol is extracted from the reaction mixture by addition of water and toluene, and isolated from the organic layer by concentration and/or by distillation of the solvent. Propofol prepared by the process of present invention may be optionally purified using high vacuum distillation.

Propofol prepared by the process according to the present invention is highly pure and is suitable for pharmaceutical use. Propofol prepared by the process of the present invention is more than 99% pure by HPLC, preferably more than 99.5% pure by HPLC, more preferably 99.9% pure by HPLC. In some embodiments, the propofol prepared by the process of the present invention is 99%-99.9%, 99%-99.5%, or 99.5%-99.9% pure by HPLC.

The starting material, 4-hydroxy-3,5-diisopropylbenzoic acid, of formula II as used in the present invention can be prepared by using prior art methods e.g. using the process reported in *Organic Process Research & Development,* 18(1), 152-156; 2014. Specifically, 4-hydroxy-3,5-diisopropylbenzoic acid may be prepared by alkylation of 4-hydroxybenzoic acid in the presence of isopropanol and an inorganic acid.

The inorganic acid may be selected from the group consisting of hydrochloric acid, perchloric acid and sulfuric acid, preferably sulfuric acid. The acid may be used as concentrated or aqueous mineral acid. The reaction mixture comprising 4-hydroxybenzoic acid, isopropanol, and an inorganic acid may be heated to a temperature of 40-70° C., until completion of the alkylation reaction. The reaction mixture may be cooled to 0° C. to ambient temperature followed by isolation of 4-hydroxy-3,5-diisopropylbenzoic acid of formula II. The resulting compound may be extracted from the reaction mixture by the addition of water and an organic solvent. The organic solvent may be selected from the group consisting of aromatic hydrocarbon solvents such as anisole, toluene; halogenated solvents such as dichloromethane, dichloroethane; ester solvents such as ethyl acetate, and mixtures thereof, preferably toluene. The resulting product may be isolated from the organic layer using conventional methods such as precipitation using acid and/or base treatment followed by filtration.

The resulting compound of formula II may be proceeded as such for the further decarboxylation reaction or purified with a solvent selected from water, an alcohol such as methanol, ethanol, isopropanol; aromatic hydrocarbon solvents such as toluene, and mixtures thereof.

In another embodiment, the invention relates to pharmaceutical compositions comprising a therapeutically effective amount of highly pure propofol prepared by the process of the present invention and a pharmaceutically acceptable excipient(s)/carrier(s). Further, the pharmaceutical composition of the invention may be a liquid suspension or a lipid emulsion, preferably an injectable composition. The active ingredient(s) and excipient(s)/carrier(s) can be formulated into compositions and dosage forms according to the method known in the art.

The therapeutically effective amount, as described above, includes the amount required to treat/alleviate the severity of symptoms associated with these ailments as decided by the persons of ordinary skill in the art.

The use of a heterocyclic base for decarboxylation, provides a time-efficient process for the commercial manufacturing of propofol and, surprisingly, avoids the need of multiple washings during the process. Another advantage of the present invention is to avoid the use of high boiling solvent during the decarboxylation reaction, which may impact the quality of the final API and requires extensive workup.

The following examples describe specific embodiments of the present invention, which will be clear and sufficient to the person skilled in the art. These examples are provided as illustration only and therefore should not be construed as limitation of the scope of the invention. Optimum reaction conditions may vary with the particular reactants or solvent used, but such conditions can be determined by one skilled in the art by routine optimization procedures.

EXAMPLES

Reference Example 1: Preparation of 4-hydroxy-3,5-diisopropylbenzoic acid (*Organic Process Research & Development,* 18(1), 152-156; 2014)

Isopropanol (95.5 g) was added to a solution of conc. sulfuric acid (250 ml) in demineralized water (17.5 ml) and stirred for 10-15 minutes. 4-Hydroxybenzoic acid (100 g) was added to the above mixture and stirred for 10-15 minutes at −10 to 0° C. followed by stirring for 16-18 hours at 40-50° C. The reaction mixture was cooled to 0-10° C., and pre-cooled toluene (500 ml) and demineralized water (1000 ml) was added. The resulting reaction mixture was stirred at 40-50° C. for 5-10 minutes and layers were separated. The aqueous layer was washed with toluene (300 ml) and organic layers were combined. Demineralized water (1000 ml) was added to the combined organic layer followed by pH adjustment with dilute sodium hydroxide between pH 9-11 and stirred for 5-10 minutes at ambient temperature. Layers were separated and dilute hydrochloric acid (70 ml conc. HCl in 140 ml water) was added to the aqueous layer and stirred for 7-8 hours at 20-30° C. The resulting solid was filtered, washed with water and dried. The product was treated with methanol and demineralised water to give 100-120 g of 4-hydroxy-3,5-diisopropylbenzoic acid.

Reference Example 2: Preparation of Propofol Using Triethylamine

To a mixture of 3,5-diisopropyl-4-hydroxybenzoic acid (90 g) in dimethylformamide (270 ml), triethylamine (205 g, 2.025 mol) was added and the reaction mixture was heated at 100-105° C. for 27 hours. The reaction mixture was cooled to 20° C. and diluted with water (900 ml) followed by addition of toluene (540 ml). 3% Diluted hydrochloric acid (450 ml) was added to the reaction mixture and stirred. The organic layer was separated and washed with 3% diluted hydrochloric acid (450 ml) and water (2×450 ml). The resulting organic layer was washed with 10% sodium chloride solution (450 ml), distilled (1-5 Mbar, 115-130° C.), degassed under reduced pressure and fractionally distilled to provide 57 g of propofol of 97.93% (purity) by HPLC.

Example 1: Preparation of Propofol Using Imidazole without Solvent 4-hydroxy-3,5-diisopropylbenzoic acid (50 g) and imidazole (7.65 g) were stirred at 20-30° C. for 15 minutes followed by stirring at 145-155° C. for 1.5-2 hours. After completion of the reaction, the reaction mixture was cooled to ambient temperature and diluted with water (125 ml). The organic layer was separated and washed with water (125 ml). The resulting organic layer was degassed and distilled (1-5 Mbar, 115-130° C.) under reduced pressure to provide 35.27 g of propofol having 99.9% purity (HPLC).

Example 2: Preparation of Propofol Using Imidazole and Toluene as the Solvent

To a mixture of 3,5-diisopropyl-4-hydroxybenzoic acid (100 g) in toluene (200 ml), imidazole (15.3 g, 0.5 mol) was added and the reaction mixture was heated at 145-155° C. for 1.5-2 hours. After completion of the reaction, the reaction mixture was cooled to ambient temperature and diluted with water (250 ml) followed by addition of toluene (500 ml). The organic layer was separated and washed with sodium bicarbonate (10 g in 200 ml water). The resulting organic layer was washed with water (250 ml), diluted hydrochloric acid (10 ml concentrated hydrochloric acid in 250 ml water) and then again with water (250 ml). The resulting organic layer was washed with water, degassed and distilled (1-5 Mbar, 115-130° C.) under reduced pressure to provide 71.31 g of propofol of 99.97% (purity) by HPLC.

Example 3: Preparation of Propofol Using Imidazole and Anisole as the Solvent

To a mixture of 3,5-diisopropyl-4-hydroxybenzoic acid (100 g) in anisole (50 ml), imidazole (15.3 g, 0.5 mol) was added and the reaction mixture was heated at 145-155° C. for 1-2 hours. After completion of the reaction, the reaction mixture was cooled to ambient temperature and diluted with water (250 ml) followed by toluene (500 ml). The organic layer was separated, washed with diluted hydrochloric acid (250 ml), and washed with water (250 ml). The resulting organic layer was concentrated under reduced pressure and then distilled (5-10 Mbar, 90-100° C.) under reduced pressure to provide 75 g of propofol having 99.8% purity (HPLC).

Example 4: Purification of Propofol

Crude propofol (100 g) was heated to 115-130° C. and fractionally distilled under reduced pressure (1-5 Mbar) at a temperature of 115-130° C. to give 92.11 g of propofol having 99.97% purity (HPLC).

The invention claimed is:

1. A process for preparing a compound of formula I,

Formula I

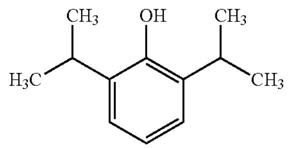

the process comprising decarboxylating 4-hydroxy-3,5-diisopropylbenzoic acid of formula II, Formula II

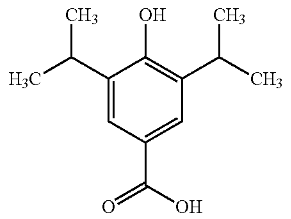

in the presence of a heterocyclic base comprising imidazole or an imidazole substituted with an alkyl group, wherein the compound of formula I has a purity of at least 99% as determined by HPLC.

2. The process as claimed in claim 1, wherein the heterocyclic base comprises imidazole.

3. The process as claimed in claim 1, wherein the decarboxylation is carried out in the presence of a solvent.

4. The process as claimed in claim 3, wherein the solvent comprises anisole, toluene, or a mixture thereof.

5. The process as claimed in claim 1, wherein the decarboxylation step is carried out without addition of a solvent.

6. The process as claimed in claim 1, wherein the decarboxylation is carried out at a temperature in the range 120-170° C.

7. The process as claimed in claim 6, wherein the decarboxylation is carried out at a temperature in the range of 145-155° C.

8. The process as claimed in claim 1, wherein the decarboxylation is carried out for 30 minutes to 3.5 hours.

9. The process as claimed in claim 1, wherein the decarboxylation is carried out for 1 hour to 2 hours.

10. A process for preparing a compound of formula I,

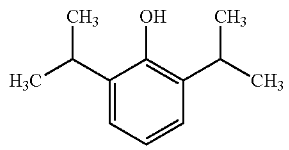

the process comprising decarboxylating 4-hydroxy-3,5-diisopropylbenzoic acid of formula II,

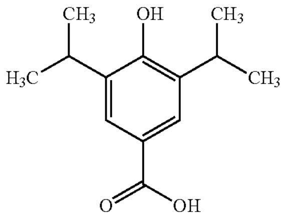

Formula II in the presence of a heterocyclic base comprising imidazole and a solvent comprising anisole.

11. The process as claimed in claim 10, wherein the decarboxylation is carried out at a temperature in the range 120-170° C.

12. The process as claimed in claim 11, wherein the decarboxylation is carried out at a temperature in the range of 145-155° C.

13. The process as claimed in claim 10, wherein the decarboxylation is carried out for 30 minutes to 3.5 hours.

14. The process as claimed in claim 13, wherein the decarboxylation is carried out for 1 hour to 2 hours.

15. The process as claimed in claim 10, wherein the compound of formula I has a purity of at least 99% as determined by HPLC.

* * * * *